United States Patent [19]
Shibasaki et al.

[11] Patent Number: 4,810,805
[45] Date of Patent: Mar. 7, 1989

[54] (2-CHLORO-3-OXO-1-ALKENYL)BICY-CLO(3.3.0)OCTANE DERIVATIVE

[75] Inventors: Masakatsu Shibasaki, Tokyo; Katsuhiko Iseki, Abiko; Masaki Shinoda, Amimachi; Chiyoko Aoki, Sagamihara; Yoshio Hayashi, Ushiku, all of Japan

[73] Assignee: Mitsubishi Chemical Industries Limited, Tokyo, Japan

[21] Appl. No.: 943,484

[22] Filed: Dec. 19, 1986

[30] Foreign Application Priority Data

Dec. 26, 1985 [JP] Japan .................... 60-292238

[51] Int. Cl.[4] .................... C07D 309/12; C07D 69/74; C07D 61/16
[52] U.S. Cl. .................... 549/421; 549/415; 549/305; 556/441; 560/119; 562/501
[58] Field of Search ............ 560/119, 105; 562/501, 562/493; 556/437, 441; 549/421, 415, 302

[56] References Cited
PUBLICATIONS

Iseki et al., Chem. Lett., (4), 559–62 (1986).

Primary Examiner—Nicky Chan
Attorney, Agent, or Firm—Oblon, Fisher, Spivak, McClelland & Maier

[57] ABSTRACT

There are disclosed a (2-chloro-3-oxo-1-alkenyl)-bicyclo[3.3.0 octene derivative represented by the formula:

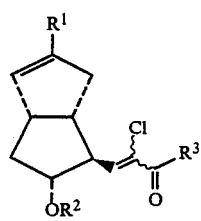

wherein $R^1$ represents $-CH_2CH_2CH_2COOR^5$, $-CH_2CH_2-O-CH_2COOR^5$, $-CH=CHCH_2COOR^5$ or $-CH_2CH_2C\equiv C-COOR^5$ group where $R^5$ in the groups represents a hydrogen atom or an alkyl group having 1 to 6 carbon atoms; $R^2$ represents a hydrogen atom, an acyl group having 1 to 7 carbon atoms, a tri(1 to 7 carbon atoms)-hydrocarbylsilyl group or a group forming an acetal bonding with an oxygen atom of a hydroxy group; $R^3$ represents a straight or branched alkyl group having 3 to 10 carbon atoms, a cycloalkyl group having 4 to 7 carbon atoms, which may be substituted by at least one alkyl group having 1 to 4 carbon atoms, a straight or branched alkenyl group having 3 to 12 carbom atoms, a straight or branched alkynyl group having 3 to 8 carbon atoms, a phenyl group or a phenoxy group which may have substituents, an alkoxy group having 1 to 6 carbon atoms or an alkyl group substituted by a cycloalkyl group having 5 to 8 carbon atoms, and a process for preparing the same which comprises reacting an aldehyde represented by the formula:

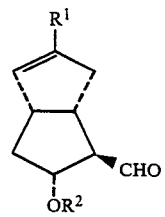

wherein $R^1$ and $R^2$ have the same meanings as defined above, with kotophosphonate represented by the formula:

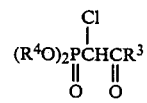

wherein $R^3$ has the same meaning as defined above and $R^4$ represents an alkyl group having 1 to 10 carbon atoms, in the presence of a base.

1 Claim, No Drawings

(2-CHLORO-3-OXO-1-ALKENYL)BICYCLO(3.3.-0)OCTANE DERIVATIVE

BACKGROUND OF THE INVENTION

This invention relates to a (2-chloro-3-oxo-1-alkenyl)-bicyclo[3.3.0]octene derivative and a process for preparing the same. This invention is to provide a novel compound available for a synthetic intermediate of prostacyclins and a process for preparing the same.

In the German Offenlegungsschrift No. 25 39 116 specification, there are disclosed a prostaglandin intermediate represented by the following formula:

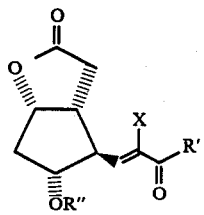

wherein R' represents a substituted or unsubstituted alkyl group, R" represents a protective group for a hydroxy group and X represents a chlorine atom or iodine atom, and a process for preparing said intermediate by reacting an aldehyde represented by the formula:

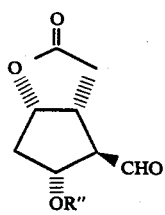

wherein R" has the same meaning as defined above, with a compound represented by the formula:

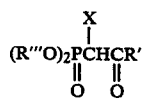

wherein R' and X have the same meanings as defined above, and R''' represents an alkyl group. Further, in the specification of Japanese Provisional Patent Publication No. 21642/1984, there is disclosed that an intermediate of the prostacyclin compound represented by the formula:

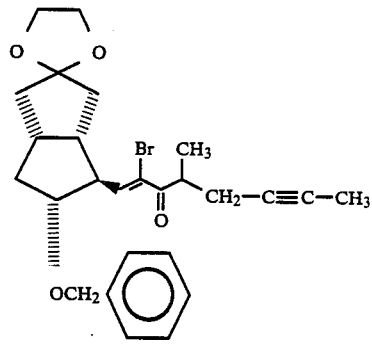

can be prepared by reacting an aldehyde represented by the formula:

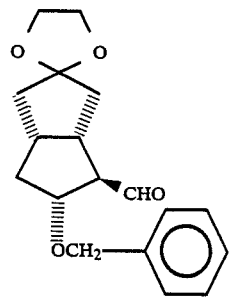

with 3-oxophosphonate represented by the formula:

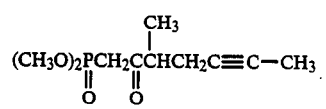

in the presence of a base and N-bromosuccinimide. However, there is no literature concerning a (2-chloro-3-oxo-1-alkenyl)bicyclo[3.3.0]octene derivative represented by the general formula (I):

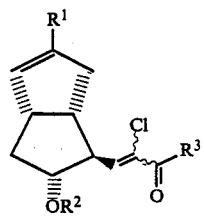

wherein $R^1$, $R^2$ and $R^3$ have the meanings as defined below, and a process for preparing the same.

SUMMARY OF THE INVENTION

The present invention is to provide a (2-chloro-3-oxo-1-alkenyl)bicyclo[3.3.0]octene derivative represented by the formula:

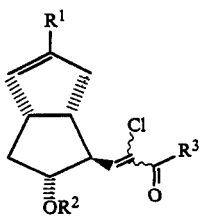
(I)

wherein R¹ represents —CH₂CH₂CH₂CH₂COOR⁵, —CH₂CH₂—O—CH₂COOR⁵, —CH=CHCH₂CH₂COOR⁵ or —CH₂CH₂C≡C—COOR⁵ group where R⁵ in the groups represents a hydrogen atom or an alkyl group having 1 to 6 carbon atoms; R² represents a hydrogen atom, an acyl group having 1 to 7 carbon atoms, a tri(1 to 7 carbon atoms)hydrocarbylsilyl group or a group forming an acetal bonding with an oxygen atom of a hydroxy group; R³ represents a straight or branched alkyl group having 3 to 10 carbon atoms, a cycloalkyl group having 4 to 7 carbon atoms, which may be substituted by at least one alkyl group having 1 to 4 carbon atoms, a straight or branched alkenyl group having 3 to 12 carbon atoms, a straight or branched alkynyl group having 3 to 8 carbon atoms, a phenyl group or a phenoxy group which may have substituents, an alkoxy group having 1 to 6 carbon atoms or an alkyl group substituted by a cycloalkyl group having 5 to 8 carbon atoms, and a process for preparing a (2-chloro-3-oxo-1-alkenyl)bicyclo[3.3.0]octene derivative represented by the formula:

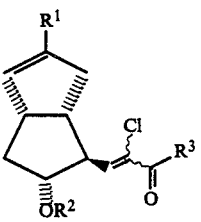
(I)

wherein R¹, R² and R³ have the same meanings as defined above, which comprises reacting an aldehyde represented by the formula:

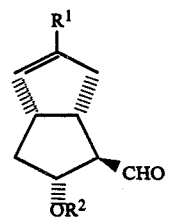
(II)

wherein R¹ represents —CH₂CH₂CH₂CH₂COOR⁵, —CH₂CH₂—O—CH₂COOR⁵, —CH=CHCH₂CH₂COOR⁵ or —CH₂CH₂C≡C—COOR⁵ group where R⁵ in the groups represents a hydrogen atom or an alkyl group having 1 to 6 carbon atoms; and R² represents a hydrogen atom, an acyl group having 1 to 7 carbon atoms, a tri(1 to 7 carbon atoms)hydrocarbylsilyl group or a group forming an acetal bonding with an oxygen atom of a hydroxy group, with ketophosphonate represented by the formula (III):

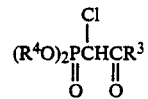
(III)

wherein R³ represents a straight or branched alkyl group having 3 to 10 carbon atoms, a cycloalkyl group having 4 to 7 carbon atoms, which may be substituted by at least one alkyl group having 1 to 4 carbon atoms, a straight or branched alkenyl group having 3 to 12 carbon atoms, a straight or branched alkynyl group having 3 to 8 carbon atoms, a phenyl group or a phenoxy group which may have substituents, an alkoxy group having 1 to 6 carbon atoms or an alkyl group substituted by a cycloalkyl group having 5 to 8 carbon atoms; and R⁴ represents an alkyl group having 1 to 10 carbon atoms, in the presence of a base.

DESCRIPTION OF THE PREFERRED EMBODIMENTS

1. Title compound

The title compound of the present invention is the (2-chloro-3-oxo-1-alkenyl)bicyclo[3.3.0]octene derivative represented by the above formula (I).

The substituent R¹ in the above formula (I) is —CH₂CH₂CH₂CH₂COOR⁵, —CH₂CH₂—O—CH₂COOR⁵, —CH=CHCH₂CH₂COOR⁵ or —CH₂CH₂C≡C—COOR⁵ and R⁵ is a hydrogen atom or an alkyl group having 1 to 6 carbon atoms. As the alkyl group having 1 to 6 carbon atoms, there may be mentioned methyl, ethyl, n-propyl, isopropyl, n-butyl, t-butyl, n-pentyl, n-hexyl and the like. R² represents a hydrogen atom, an acyl group having 1 to 7 carbon atoms, a tri(1 to 7 carbon atoms)hydrocarbylsilyl group or a group forming an acetal bonding with an oxygen atom of a hydroxy group. Here, as the acyl group having 1 to 7 carbon atoms, there may be mentioned, for example, acetyl, propionyl, n-butyryl, isobutyryl, n-valeryl, isovaleryl, caproyl, enanthyl, benzoyl, etc., preferably acetyl, benzoyl, etc. As the tri(1 to 7 carbon atoms)hydrocarbylsilyl group, there may be mentioned, for example, tri(1 to 4 carbon atoms)alkylsilyl such as trimethylsilyl, triethylsilyl, tert-butyldimethylsilyl groups; diphenylalkylsilyl such as a tertbutyldiphenylsilyl group; a tribenzylsilyl group; a dimethyl(2,4,6-tri-tert-butylphenoxy)silyl group; and the like. As the groups forming an acetal bonding with an oxygen atom of a hydroxy group, there may be mentioned, for example, methoxymethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofuranyl, 4-(4-methoxytetrahydropyranyl) group or a 6,6-dimethyl-3-oxa-2-oxobicyclo[3.1.0]hex-4-yl group. Of these groups, 2-tetrahydropyranyl, 2-tetrahydrofuranyl, 1-ethoxyethyl, 2-methoxy-2-propyl, (2-methoxyethoxy)methyl, 4-(4-methoxytetrahydropyranyl), 6,6-dimethyl-3-oxa-2-oxobicyclo[3.1.0]hex-4-yl groups are preferred.

R³ represents a straight or branched alkyl group having 3 to 10 carbon atoms, an unsubstituted or substituted cycloalkyl group having 4 to 7 carbon atoms substituted by an alkyl group having 1 to 4 carbon atoms, a straight or branched alkenyl group having 3 to 12 carbon atoms, a straight or branched alkynyl group having 3 to 8 carbon atoms, a phenyl group or a phenoxy group each of which may be substituted by substituents, an alkoxy group having 1 to 6 carbon atoms, or a substituted alkyl group having 1 to 3 carbon atoms substituted by a cycloalkyl group having 5 to 8 carbon atoms. Here, as the straight or branched alkyl groups having 3 to 10 carbon atoms, there may be mentioned n-propyl, n-butyl, n-pentyl, 1-methylpentyl, 2-methylpentyl, 1,2-dimethylpentyl, n-hexyl, 1-methylhexyl, 2-methylhexyl, 1,2-dimethylhexyl, n-heptyl, n-octyl, n-nonyl, n-decyl, etc., preferably n-pentyl, 1-methylpentyl, 2-methylpentyl, 1,2-dimethylpentyl, n-hexyl, 1-methylhexyl, 2-methylhexyl, etc.

As the unsubstituted cycloalkyl groups having 4 to 7 carbon atoms or substituted by at least one alkyl group having 1 to 4 carbon atoms, there may be mentioned cyclobutyl, 1-propylcyclobutyl, 1-butylcyclobutyl, 1-pentylcyclobutyl, 2-methylcyclobutyl, 2-propylcyclobutyl, 3-ethylcyclobutyl, 3-propylcyclobutyl, 2,3,4-triethylcyclobutyl, cyclopentyl, 2-pentylcyclopentyl, 2,2-dimethylcyclopentyl, 3-ethylcyclopentyl, 3-propylcyclopentyl, 3-butylcyclopentyl, 3-tert-butylcyclopentyl, (1-methyl-3-propyl)cyclopentyl, (2-methyl-3-propyl)cyclopentyl, (2-methyl-4-propyl)cyclopentyl, cyclohexyl, 3-ethylcyclohexyl, 3-isopropylcyclohexyl, 4-methylcyclohexyl, 4-ethylcyclohexyl, 4-propylcyclohexyl, 4-tert-butylcyclohexyl, 2,6-dimethylcyclohexyl, 2,2-dimethylcyclohexyl, (2,6-dimethyl-4-propyl)cyclohexyl, cycloheptyl, etc., preferably cyclopentyl, cyclohexyl, etc.

As the straight or branched alkenyl groups having 3 to 12 carbon atoms, there may be mentioned, for example, allyl, 3-butenyl, 2-butenyl, 3-methyl-2-butenyl, 4-pentenyl, 3-pentenyl, 4-methyl-3-pentenyl, 2-pentenyl, 5-hexenyl, 4-hexenyl, 3-methyl-4-hexenyl, 5-methyl-2-hexenyl, 2,5-dimethyl-3-hexenyl, 6-heptenyl, 5-heptenyl, 2-ethyl-5-heptenyl, 2,6-dimethyl-5-heptenyl, 7-octenyl, 8-nonenyl, 9-decenyl, 10-undecenyl, 11-dodecenyl, etc., preferably 3-pentenyl, 2,6-dimethyl-5-heptenyl, etc.

As the straight or branched alkynyl groups having 3 to 8 carbon atoms, there may be mentioned propargyl, 2-butynyl, 3-butynyl, 2-methyl-3-butynyl, 2-ethyl-3-butynyl, 4-pentynyl, 3-pentynyl, 1-ethyl-3-pentynyl, 1-methyl3-pentynyl, 2-methyl-3-pentynyl, 1,2-dimethyl-3-pentynyl, 1,1-dimethyl-3-pentynyl, 2,2-dimethyl-3-pentynyl, 3-hexynyl, 1-methyl-3-hexynyl, 2-methyl-3-hexynyl, 1,2-dimethyl 3-hexynyl, 1,1,Tdimethyl-3-hexynyl, 2,2-dimethyl-3-hexynyl, 4-heptynyl, 5-octynyl, etc., preferably 1-methyl -3-pentynyl, 1-methyl-3-hexynyl, 2-methyl-3-hexynyl, etc.

As the alkyl groups of the substituted alkyl group having 1 to 3 carbon atoms, they may be any of straight or branched, and may be mentioned, for example, methyl, ethyl, n-propyl, isopropyl, etc. These alkyl groups may be substituted by a phenyl group; a phenoxy group; an alkoxy group having 1 to 6 carbon atoms such as methoxy, ethoxy, n-propoxy, n-butoxy, isobutoxy, tert-butoxy, n-pentoxy, n-hexoxy, etc.; or a cycloalkyl group having 5 to 8 carbon atoms such as cyclopentyl, cyclohexyl, etc. As the substituted alkyl groups having 1 to 3 carbon atoms, of these, preferred are alkyl groups having 1 to 2 carbon atoms substituted by a phenoxy group or a phenyl group, which phenoxy or phenyl group may be substituted by, for example, a fluorine atom, a chlorine atom, methyl, ethyl or trifluoromethyl groups; or propoxymethyl, 2-ethoxyethyl, 2-propoxyethylbutoxymethyl, (2-ethoxy1-methyl)ethyl, cyclohexylmethyl, 1-cyclohexylethyl, 2-cyclohexylethyl, etc.

$R^4$ represents an alkyl group having 1 to 10 carbon atoms, and they may be mentioned methyl, ethyl, n-propyl, isopropyl, tert-butyl, n-butyl, isobutyl, sec-butyl, n-pentyl, neopentyl, n-hexyl, cyclohexyl, 4-methylcyclohexyl, 2,6-dimethylcyclohexyl, 2,4,6-trimethylcyclohexyl, 4-tert-butylcyclohexyl, etc.

As the specific examples of the present compounds, there may be mentioned (1) 3-(4-ethoxycarbonyl-1-butynyl)-6-exo-(2-chloro-3-oxo-1-octynyl)-7-endo-tetrahydropyranyloxybicyclo[3.3.0]oct-2-ene (2) 3-(4-ethoxycarbonyl-1-butynyl)-6-exo-(2-chloro-4-methyl-3-oxo-1-octenyl)-7-endo-tetrahydropyranyloxybicyclo[3.3.0]oct-2-ene (3) 3-(4-ethoxycarbonyl-1-butynyl)-6-exo-(2-chloro-5-methyl-3-oxo-1-octenyl)-7-endo-tetrahydropyranyloxybicyclo [3.3.0]oct-2-ene (4) 3-(4-methoxycarbonyl-1-butynyl)-6-exo-(2-chloro-3-cyclohexyl-3-oxo-1-propenyl)-7-endo-(1-methyl-1-methoxyethyloxy)-bicyclo[3.3.0]oct-2-ene (5) 3-(4-methoxycarbonyl-1-butynyl)-6-exo-(2-chloro-3-cyclopentyl-3-oxo-1-propenyl)-7-endo-tert-butyldimethylsiloxybicyclo[3.3.0]oct-2-ene (6) 3-(4-ethoxycarbonyl-1-butynyl)-6-exo-(2-chloro-4-methyl-3-oxo-1-octen-6-ynyl)-7-endo-tetrahydropyranyloxybicyclo[3.3.0]oct-2-ene (7) 3-(4-ethoxycarbonyl-1-butynyl)-6-exo-(2-chloro-4-methyl-3-oxo-1-nonen-6-ynyl)-7-endo-tetrahydropyranyloxybicyclo[3.3.0]oct-2-ene (8) 3-(4-ethoxycarbonyl-1-butynyl)-6-exo-(2-chloro-5-methyl-3-oxo-1-nonenyl)-7-endo-acetoxybicyclo[3.3.0]oct-2-ene (9) 3-(4-methoxycarbonyl-1-butynyl)-6-exo-(2-chloro-5-methyl-3-oxo-1-nonen-6-ynyl)-7-endo-tetrahydropyranyloxybicyclo[3.3.0]oct-2-ene

(10) 3-{2-(tert-butoxycarbonylmethoxy)ethyl}-6-exo-(2-chloro-3-oxo-1-octynyl)-7-endo-tetrahydropyranyloxybicyclo[3.3.0]oct-2-ene

(11) 3-{2-(tert-butoxycarbonylmethoxy)ethyl}-6-exo-(2-chloro-4-methyl-3-oxo-1-octen-6-ynyl)-7-endo-tetrahydropyranyloxybicyclo[3.3.0]oct-2-ene

(12) 3-{2-(tert-butoxycarbonylmethoxy)ethyl}-6-exo-(2-chloro-4-methyl-3-oxo-1-nonen-6-ynyl)-7-endo-tetrahydropyranyloxybicyclo[3.3.0]oct-2-ene

(13) 3-(4-ethoxycarbonyl-1-butynyl)-6-exo-(2-chloro-3-oxo-1-octenyl)-7-endo-tetrahydropyranyloxybicyclo[3.3.0]-oct-2-ene

(14) 3-(4-ethoxycarbonyl-3-butynyl)-6-exo-(2-chloro-4-methyl-3-oxo-1-nonen-6-ynyl)-7-endo-tetrahydropyranyloxybicyclo[3.3.0]oct-2-ene

(15) 3-(4-ethoxycarbonylbutyl)-6-exo-(2-chloro-3-oxo-1-octenyl)-7-endo-tetrahydropyranyloxybicyclo[3.3.0]oct-2-ene

(16) 3-(4-ethoxycarbonylbutyl)-6-exo-(2-chloro-3-cyclopentyl-3-oxo-1-propenyl)-7-end 2-ene and the like.

2. Starting materials and preparative method of the title compounds

The aldehyde represented by the above formula (II) used as the starting material of the present invention can be led from Corey's lactone with extremely good efficiency (see Preliminary text for lectures in 104th Annual Meeting (at Sendai) in Pharmaceutical Society of Japan, p. 282; and Japanese Provisional Patent Publication No. 202821/1985 and Japanese Patent Applications No. 30487/1985 and No. 204539/1985).

The ketophosphonate represented by the above formula (III) can be easily prepared by reacting ketophosphonate represented by the formula (IV)

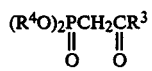  (IV)

wherein $R^3$ and $R^4$ have the same meanings as defined above, with N-chlorosuccinic acid imide in the presence of sodium hydride (see the following Reference example).

The compound of the present invention can be synthesized by reacting the aldehyde represented by the above formula (II) with the ketophosphonate represented by the above formula (III) in the presence of a base.

As the base to be used, there may be mentioned n-butyllithium, lithium diisopropylamide, sodium hydride, sodium amide, potassium tert-butoxide, etc. An amount of the base to be used may preferably be 0.5 to 1.0 equivalent to the reagent represented by the formula (III). An amount of the reagent represented by the formula (III) may preferably be 1.0 to 10 equivalents to the aldehyde represented by the formula (II). The reaction is carried out in a solvent and there may be used organic solvents of dimethylformamide, dimethylsulfoxide; ethers such as ethyl ether, tetrahydrofuran, 1,2-dimethoxyethane, etc.; aromatic organic solvents such as benzene, toluene, xylene, etc.; or aliphatic hydrocarbons such as pentane, hexane, cyclohexane, decaline, etc., as singly or in combination therewith. The reaction is carried out at $-78°$ C. to $100°$ C., preferably $-20°$ C. to $40°$ C. 3. Availability The compound (I) of the present invention is useful as an intermediate for synthesis of prostacyclin analogues, and it can be led to the prostacyclin analogue by the route shown below.

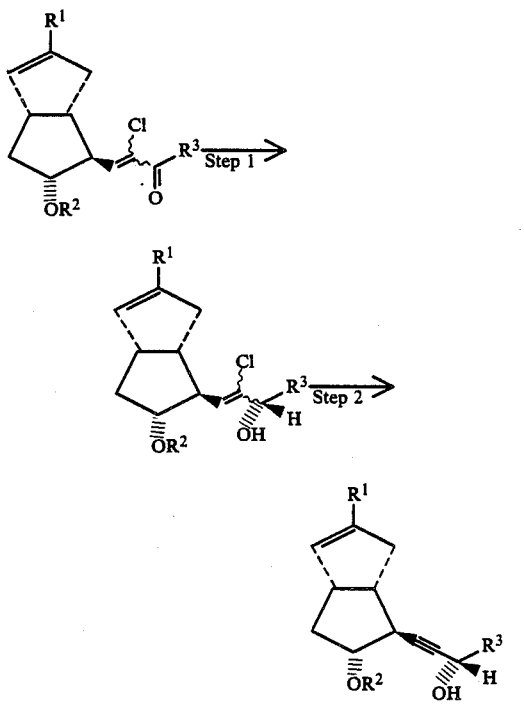

The step 1 is a step to obtain the compound (V) by reducing the compound (I). As the reducing agent, those not to reduce $R^1$ are preferred and may include, for example, sodium borohydride, zinc borohydride or lithium trialkylborohydride such as tri-sec-butylborohydride, and di-isobutylaluminum hydride modified by 2,6-di-tert-butyl-4-methylphenol, or lithium aluminum hydride modified by 1,1'-bi-2-naphthol and a lower alcohol such as ethanol, or the like. As the reaction solvent, there may be mentioned lower alcohols such as methanol, ethanol, etc.; ethers such as ethyl ether, tetrahydrofuran, dioxane, etc.; aromatic hydrocarbons such as benzene and toluene; and the like. An amount of the reducing agent to be used is preferably 0.5 to 30 equivalents, particularly preferably 1 to 10 equivalents based on the starting compound (I). The reaction temperature is $-150°$ C. to $80°$ C., preferably $-100°$ C. to $30°$ C.

The step 2 is a step to produce the compound (VI) by reacting the compound (V) with a base. As the base, n-butyllithium, sodium methoxide, sodium ethoxide, potassium tert-butoxide, etc. are preferably used, and an amount thereof is 1 to 100 equivalents based on the compound (V). As the reaction solvent, there may be used dimethylsulfoxide, benzene, toluene, ethyl ether, tetrahydrofuran, 1,2-dimethoxyethane, methanol, ethanol, water, etc. as alone or a mixed solvent thereof. The reaction temperature is $-78°$ C. to $150°$ C., preferably $-20°$ C. to $50°$ C.

EXAMPLES

In the following, the present invention will be explained in detail by referring to the Examples and Reference examples.

EXAMPLE 1

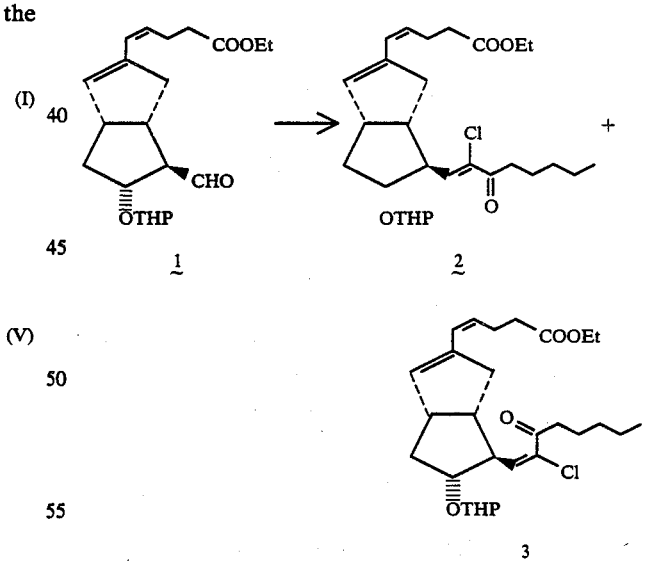

Under argon gas atmosphere, 60% sodium hydride (55 mg, 1.38 mmol) was suspended in anhydrous DME (dimethoxyethane, 5 ml), and to the suspension was added at room temperature dimethyl(1-chloro-2-oxoheptyl)phosphonate (420 mg, 1.64 mmol) dissolved in anhydrous DME (5 ml) and the mixture was stirred at the same conditions for 1 hour. To the mixture was added the aldehyde 1 (330 mg, 0.91 mmol) dissolved in anhydrous DME (5 ml) and the mixture was stirred at room temperature for 24 hours. A saturated aqueous ammonium chloride solution was added to the reaction mixture and the reaction mixture was extracted by ethyl ether. The organic layer was dried over anhydrous magnesium sulfate and the solvent was evaporated under reduced pressure. The obtained residue was purified through silica gel column chromatography to obtain the product 3 (218 mg, 49%) as a lower polarity component and the product 2 (139 mg, 31%) as a higher polarity component, respectively.

(2)

IR (neat): 2930, 1735, 1690, 1610 cm$^{-1}$.
NMR δ (CDCl$_3$): 6.85 (d, J=10.4 Hz, 1H), 6.00 (d, J=11 Hz, 1H), 5.58 (s, 1H), 5.35 (m, 1H), 4.60 (m, 1H), 4.12 (q, J=7.1 Hz, 2H), 1.27 (t, J=7.1 Hz, 3H) ppm.
Mass m/z: 492 [M+], 410, 408, 216, 117, 85.

(3)

IR (neat): 2930, 1735, 1693, 1600 cm$^{-1}$.
NMR δ (CDCl$_3$): 6.03 (2d, J=11 Hz, 2H), 5.60 (s, 1H), 5.35 (m, 1H), 4.68 (m, 1H), 4.16 (q, J=7.1 Hz, 2H), 1.27 (t, J=7.1 Hz, 3H) ppm.
Mass m/z: 492 [M+], 449, 447, 410, 408, 216, 117, 85.

EXAMPLE 2

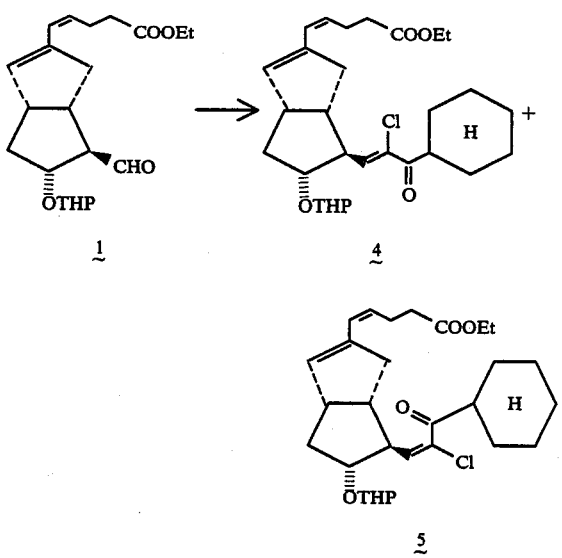

According to the same procedures as in Example 1, from the aldehyde 1 (2.19 g, 6.04 mmol) and dimethyl(1-chloro-2-oxo-2-cyclohexylethyl)phosphonate (3.24 g, 12.06 mmol), the product 5 (1.05 g, 34%) as a lower polarity component and the product 4 (1.33 g, 44%) as a higher polarity component were obtained, respectively.

(4)

IR (neat): 2940, 1725, 1680, 1608 cm$^{-1}$.
NMR δ (CDCl$_3$): 6.68 (d, J=9.8 Hz, 1H), 5.86 (d, J=10.8 Hz, 1H), 5.50 (s, 1H), 5.25 (m, 1H), 4.03 (q, J=7 Hz, 2H), 1.19 (t, J=7 Hz, 3H) ppm.
Mass m/z: 420 [M+ −84], 260, 191, 85.

(5)

IR (neat): 2940, 1730, 1685, 1605 cm$^{-1}$.
NMR δ (CDCl$_3$) 5.90 (2d, J=10 Hz, 2H), 5.50 (s, 1H), 5.25 (m, 1H), 4.06 (q, J=6.6 Hz, 2H), 1.23 (t, J=6.6 Hz, 3H) ppm.
Mass m/z: 504 [M+], 459, 420, 260, 191, 85.

EXAMPLE 3

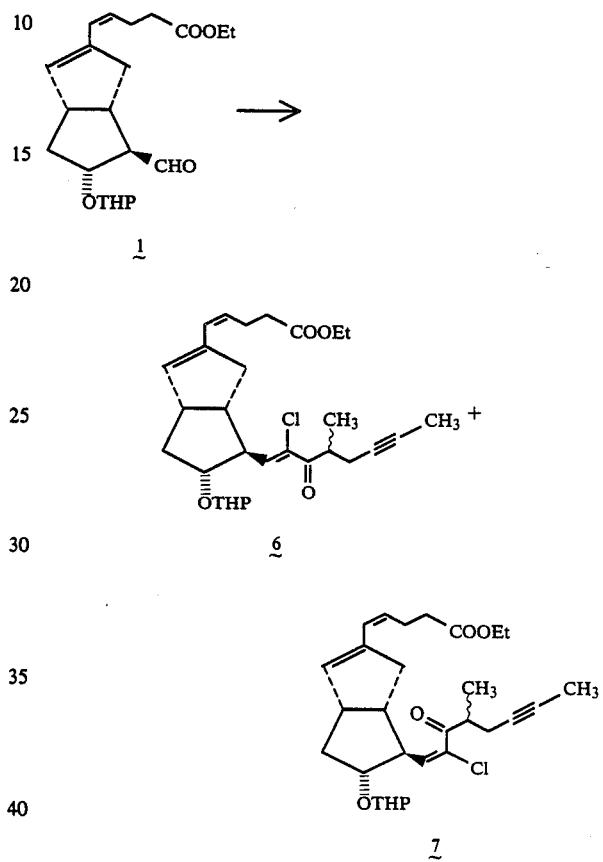

According to the same procedures as in Example 1, from the aldehyde 1 (166 mg, 0.44 mmol) and dimethyl(1-chloro-3-methyl-2-oxo-5-heptynyl)phosphonate (245 mg, 0.92 mmol), the product 7 (50 mg, 23%) as a lower polarity component and the product 6 (75 mg, 34%) as a higher polarity component were obtained, respectively.

(6)

NMR δ (CDCl$_3$): 6.87 (d, J=10 Hz, 1H), 5.90 (d, J=12 Hz, 1H), 5.4–5.6 (m, 1H), 5.0–5.4 (m, 1H), 4.3–4.7 (m, 1H), 4.08 (q, J=7 Hz, 2H), 1.1–1.4 (m, 6H) ppm.
IR (neat): 1730, 1685, 1605, 1150, 1030 cm$^{-1}$.
Mass m/z: 502 [M+], 457, 418, 365.

(7)

NMR δ (CDCl$_3$) 5.98 (d, J=10 Hz, 1H), 5.85 (d, J=12 Hz, 1H), 5.3–5.5 (m, 1H), 5.0–5.4 (m, 1H), 4.4–4.6 (m, 1H), 4.04 (q, J=7 Hz, 2H), 1.1–1.4 (m, 6H) ppm.
IR (neat): 1730, 1690, 1440, 1130, 1030 cm$^{-1}$. Mass m/z: 502 [M+], 457, 418, 365.

Example 4

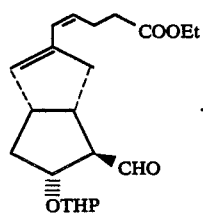

1

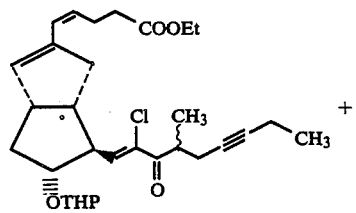

8

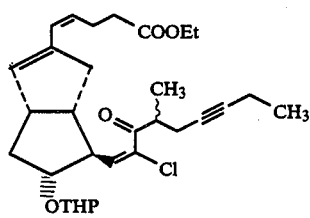

9

According to the same procedures as in Example 1, from the aldehyde 1 (1.82 g, 5.02 mmol) and dimethyl (1-chloro-3-methyl-2-oxo-5-octynyl)phosphonate (2.85 g, 10.2 mmol), the product 9 (956 mg, 37%) as a lower polarity component and the product 8 (1.27 g, 49%) as a higher polarity component were obtained, respectively.

(8)

NMR δ (CDCl$_3$): 6.76 (d, J=9.6 Hz, 1H), 5.88 (d, J=11.2 Hz, 1H), 5.54 (s, 1H), 5.25 (m, 1H), 4.53 (m, 1H), 4.06 (q, J=6.4 Hz, 2H) ppm.

Mass m/z: 516 [M+], 432, 388, 234, 85.

(9)

NMR δ (CDCl$_3$): 5.96 (2d, J=10.6 Hz, 2H), 5.54 (s, 1H), 5.25 (m, 1H), 4.60 (m, 1H), 4.10 (q, J=6.8 Hz, 2H) ppm.

Mass m/z: 516 [M+], 432, 388, 260. 85.

EXAMPLE 5

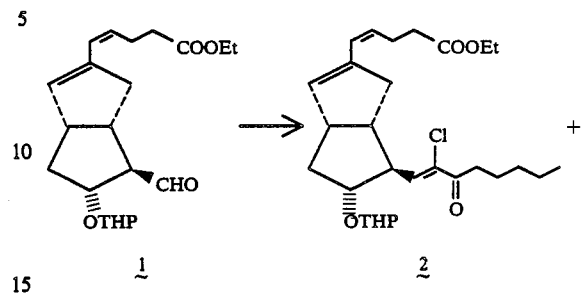

1      2

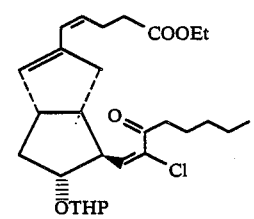

3

According to the same procedures as in Example 1, from the aldehyde 1 (115 mg, 0.32 mmol) and diisopropyl(1-chloro-2-oxoheptyl)phosphonate (200 mg, 0.64 mmol), the product 3 (32.1 mg, 21%) as a lower polarity component and the product 2 (89.3 mg, 57%) as a higher polarity component were obtained, respectively.

EXAMPLE 6

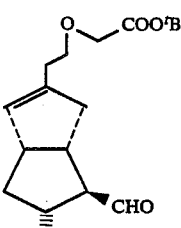

10

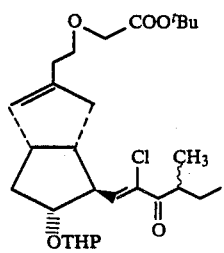

11

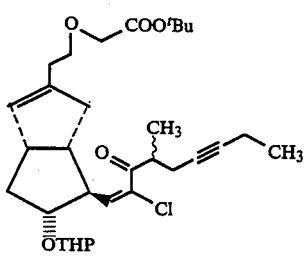

12

According to the same procedures as in Example 1, from the aldehyde 10 (1.80 g, 4.56 mmol) and dimethyl (1-chloro-3-methyl-2-oxo-5-heptynyl)phosphonate (2.56 g, 9.12 mmol), the product 12 (569 mg, 23%) as a lower polarity component and the product 11 (660 mg, 26%) as a higher polarity component were obtained, respectively.

(11)

IR (neat): 2940, 1745, 1690, 1610, 1150 cm$^{-1}$.

NMR δ (CDCl$_3$): 6.74 (d, J=10.6 Hz, 1H), 5.32 (s, 1H), 4.52 (m, 1H), 3.90 (s, 2H), 1.48 (s, 9H) ppm.

Mass m/z: 464 [M$^+$−84], 408, 364, 297, 222, 85.

(12) IR (neat): 2940, 1740, 1690, 1605, 1150 cm$^{-1}$.

NMR δ (CDCl$_3$): 5.90 (d, J=10 Hz, 1H), 5.32 (s, 1H), 4.51 (m, 1H), 3.91 (s, 2H), 1.47 (s, 9H) ppm.

Mass m/z: 464 [M$^+$−84], 408, 222.

EXAMPLE 7

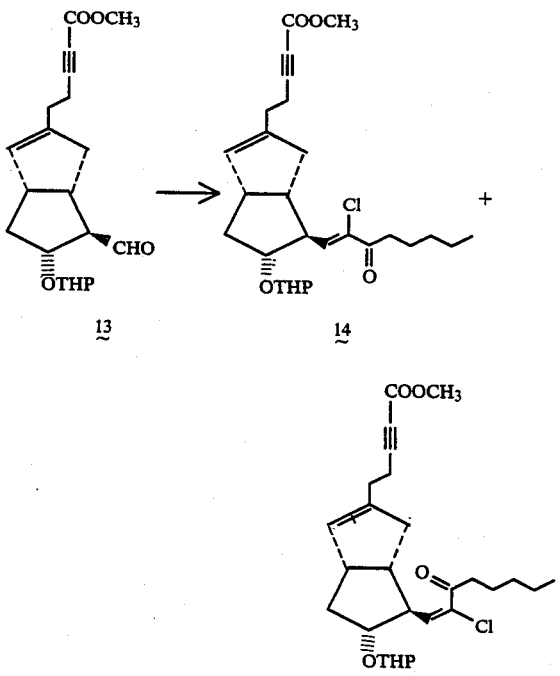

According to the same procedures as in Example 1, from the aldehyde 13 (142 mg, 0.41 mmol) and dimethyl(1chloro-2-oxoheptyl)phosphonate (210 mg, 0.82 mmol), the product 15 (93 mg, 48%) as a lower polarity component and the product 14 (91 mg, 47%) as a higher polarity component were obtained, respectively.

(14) IR (neat): 2940, 2230, 1710, 1600, 1250 cm$^{-1}$.

NMR δ (CDCl$_3$): 6.75 (d, J=9.8 Hz, 1H), 5.32 (s, 1H), 4.52 (m, 1H), 3.72 (s, 3H) ppm.

(15)

IR (neat): 2940, 2230, 1710, 1610, 1255 cm$^{-1}$.

NMR δ (CDCl$_3$) 5.89 (d, J=11 Hz, 1H), 5.28 (s, 1H), 4.53 (m, 1H), 3.72 (s, 3H) ppm.

REFERENCE EXAMPLE 1

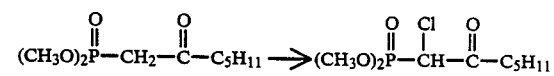

Under argon gas atmosphere, 60% sodium hydride (1.8 g, 45.0 mmol) was suspended in anhydrous DME (10 ml) and under ice-cooling, to the suspension was added dimethyl(2-oxoheptyl)phosphonate (5.0 g, 22.5 mmol) dissolved in anhydrous DME (40 ml) and the mixture was stirred at the same conditions for 30 minutes. To the mixture was added N-chlorosuccinimide (3.0 g, 22.5 mmol) and the mixture was stirred at room temperature for 2 hours. To the reaction mixture was then added a saturated aqueous ammonium chloride solution and the reaction mixture was extracted with ethyl acetate. The organic layer was dried over anhydrous magnesium sulfate and the solvent was evaporated under reduced pressure. The obtained residue was purified through silica gel column chromatography and further evaporated under reduced pressure to obtain dimethyl(1-chloro-2-oxoheptyl)phosphonate (4.4 g, 76%).

IR (neat): 2950, 1725, 1460, 1265, 1040 cm$^{-1}$.

NMR δ (CDCl$_3$): 4.56 (d, J=17 Hz, 1H), 3.90 (d, J=11 Hz, 6H), 2.77 (m, 2H) ppm.

REFERENCE EXAMPLE 2

According to the same procedures as in Reference example 1, the following compounds were synthesized. In Table 1, yields and spectrum data of the compounds are shown.

TABLE 1

| | Yield | Spectrum data | |
|---|---|---|---|
| (i-C$_3$H$_7$O)$_2$P(O)CH(Cl)C(O)—C$_5$H$_{11}$ | 52% | IR (neat): | 2950, 1710, 1250, 990 cm$^{-1}$ |
| | | NMRδ (CDCl$_3$): | 4.78(m, 2H), 4.43(d, J=17.2Hz, 1H), 2.78(m, 2H), 1.40(d, J=6Hz, 12H) ppm |
| | | Mass m/z: | 314, 3R[M$^+$], 255, 253, 216, 214, 172, 130 |
| (CH$_3$O)$_2$P(O)CH(Cl)C(O)CH(CH$_3$)CH$_2$C≡C—CH$_3$ <br> b.p. 150–156° C./0.08 mm | 61% | IR (neat): | 2970, 1715, 1265, 1030 cm$^{-1}$ |
| | | NMRδ (CDCl$_3$): | 4.88(d, J=17.6Hz, ½H), 4.68(d, J=16.8Hz, ½H), 3.88(d, J=10.8Hz, 3H), 3.86(d, J=11Hz, 3H), 3.25(m, 1H), 2.37(m, 2H), 1.77(t, J=2.5Hz, 3H), 1.24(d, J=7.2Hz, 3/2H), 1.18(d, J=7.2Hz, 3/2H) ppm |
| | | Mass m/z: | 269, 267[M$^+$ + 1], 231, 160, 158 |
| (CH$_3$O)$_2$P(O)CH(Cl)C(O)CH(CH$_3$)CH$_2$C≡C—C$_2$H$_5$ | 78% | IR (neat): | 2980, 1725, 1025 cm$^{-1}$ |
| | | NMRδ (CDCl$_3$): | 4.96(d, J=17.8Hz, ½H), 4.73(d, J=17.0Hz, ½H), 3.94(d, J=11.3Hz, 3H), 3.88(d, J=11.3Hz), 3.27(m, 1H) ppm |
| | | Mass m/z: | 283, 281[M$^+$ + 1], 245, 158 |
| (CH$_3$O)$_2$P(O)CH(Cl)C(O)—C$_6$H$_{11}$ <br> b.p. 124–125° C./0.03 mm | 77% | IR (neat): | 2940, 1720, 1265, 1040 cm$^{-1}$ |
| | | NMRδ (CDCl$_3$): | 4.66(d, J=17Hz, 1H), 3.92(d, J=10.8Hz, 6H), 2.94(m, 1H), 1.00~2.20(m, 10H) ppm |
| | | Mass m/z: | 2.71, 270, 269, 268[M$^+$], 233, 160, 158 |

Reference examples 3 to 6 shown below exhibit examples to synthesize prostacyclin analogue compounds using the compounds of the present invention as starting materials.

REFERENCE EXAMPLE 3

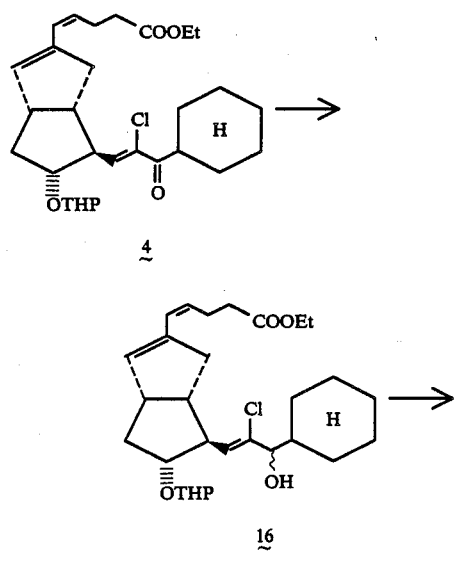

-continued

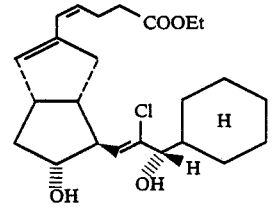

α,β-Unsaturated ketone 4 (1.32 g, 2.61 mmol) was dissolved in methanol (50 ml), and to the solution was added at −25° C. an excess amount of sodium borohydride and the mixture was stirred for 1 hour. After addition of acetone to the mixture to stop the reaction, a saturated aqueous ammonium chloride solution was added to the mixture. After evaporation of methanol, the remaining aqueous layer was extracted by ethyl ether and the extract was condensed under reduced pressure to obtain crude alcohol 16. This crude alcohol was dissolved in a 65% aqueous acetic acid solution and the solution was stirred at 50° C. for 2 hours under heating. After cooling the reaction mixture, it was poured into an aqueous NaHCO$_3$ solution, extracted by ethyl acetate and dried over anhydrous magnesium sulfate. The solvent was evaporated to obtain crude product. This crude product was purified through silica gel column chromatography to obtain the 15S-diol derivative 17 (630 mg, 57%) as a higher polarity component.

IR (neat): 3390, 2920, 1730 cm$^{-1}$.

NMR δ (CDCl$_3$) 5.84 (d, J=10.7 Hz, 1H), 4.95–5.65 (m, 3H), 4.00 (q, J=6.9 Hz, 2H), 1.20 (t, J=6.9 Hz, 3H) ppm. Mass m/z: 422 [M$^+$], 406, 404, 360, 191, 117.

REFERENCE EXAMPLE 4

According to the same procedures as in Reference example 3, the following compounds were synthesized. In Table 2, yields and spectrum data of the compounds are shown.

TABLE 2

| Compound | Yield | Spectrum data | |
|---|---|---|---|
| (structure with COOEt, Cl, CH₃, CH₃, OH, OH) | 53% | IR (neat):<br>NMRδ (CDCl₃):<br><br><br>Mass m/z: | 3400, 2930, 1730 cm$^{-1}$<br>5.97(d, J=11Hz, 1H),<br>5.10–5.85(m, 3H),<br>4.11(q, J=7.2Hz, 2H) ppm<br>404, 402[M$^+$ − 18], 117 |
| (structure with COOEt, Cl, CH₃, CH₃, OH, OH) | 49% | IR (neat):<br>NMRδ (CDCl₃):<br><br><br>Mass m/z: | 3400, 2940, 1730 cm$^{-1}$<br>5.98(d, J=11.6Hz, 1H),<br>5.10–5.84(m, 3H),<br>4.12(q, J=7.2Hz, 2H) ppm<br>418, 416[M$^+$ − 18], 321<br>234, 117 |
| (structure with COO$^t$Bu, Cl, CH₃, CH₃, OH, OH) | 52% | IR (neat):<br>NMRδ (CDCl₃):<br><br><br><br>Mass m/z: | 3400, 2920, 1745, 1130 cm$^{-1}$<br>5.62(d, J=9Hz, 1H),<br>5.33(s, 1H),<br>3.88(s, 2H),<br>1.48(s, 9H) ppm<br>413, 357, 281, 57 |

REFERENCE EXAMPLE 5

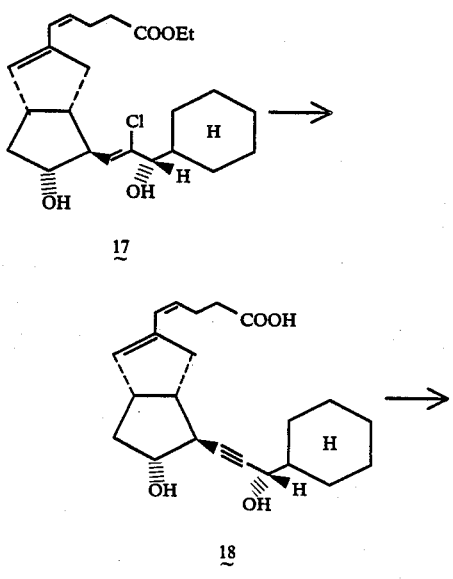

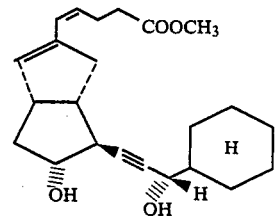

Under argon gas atmosphere, potassium t-butoxide (1.66 g, 14.8 mmol) was suspended in anhydrous THF (45 ml). At room temperature, the diol 17 (628 mg, 1.48 mmol) dissolved in anhydrous THF (30 ml) was added to the suspension and the mixture was stirred at the same conditions for 3 hours. The pH of the mixture was adjusted to 4 to 5 with 2N hydrochloric acid, and after the mixture was extracted with ethyl acetate and then washed with water, the extract was dried over anhydrous magnesium sulfate. After evaporation of the solvent, the obtained carboxylic acid 18 was treated with diazomethane without purification, the reaction mixture was purified through silica gel column chromatography to obtain the methyl ester 19 (249 mg, 45%).

IR (neat): 3360, 2240, 1735 cm$^{-1}$.
NMR δ (CDCl₃) 5.92 (d, J=11.4 Hz, 1H), 5.45 (s, 1H), 5.25 (m, 1H), 3.60 (s, 3H) ppm.
Mass m/z: 372 [M$^+$], 354, 336.

REFERENCE EXAMPLE 6

According to the same procedures as in Reference example 5, the following compounds were synthesized.

In Table 3, yields and spectrum data of the compounds are shown.

TABLE 3

| Compound | Yield | Spectrum data |
|---|---|---|
| (structure with COOCH$_3$, CH$_3$, CH$_3$, OH, OH) | 74% | IR(neat): 3390, 2240, 1735 cm$^{-1}$<br>NMRδ(CDCl$_3$):<br>5.88(d,J=11Hz,1H),<br>5.48(s,1H),<br>5.35(m,1H),<br>3.70(s,3H)ppm<br>Mass m/z: 370[M$^+$], 352, 334, 117 |
| (structure with COOCH$_3$, CH$_3$, CH$_3$, OH, OH) | 69% | IR(neat): 3380, 2230, 1735 cm$^{-1}$<br>NMRδ(CDCl$_3$):<br>5.87(d,J=11Hz,1H),<br>5.48(s,1H),<br>5.30(m,1H),<br>3.67(s,3H)ppm<br>Mass m/z: 384[M$^+$], 366, 351, 337, 117 |
| 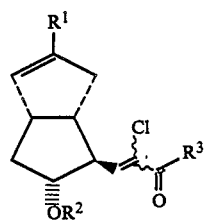 | 78% | IR(neat): 3400, 2940, 2240, 1755, 1140 cm$^{-1}$<br>NMRδ(CDCl$_3$):<br>5.32(s,1H),<br>4.01(s,2H),<br>3.70(s,3H)ppm<br>Mass m/z: 388[M$^+$], 371, 223, 115 |

We claim:

1. A (2-chloro-3-oxo-1-alkenyl)bicyclo[3.3.0]octene derivative represented by the formula:

wherein $R^1$ represents —CH$_2$CH$_2$CH$_2$CH$_2$COOR$^5$, —CH$_2$CH$_2$—O—CH$_2$COOR$^5$, —CH=CHCH$_2$CH$_2$COOR$^5$ or —CH$_2$CH$_2$C≡C—COOR$^5$ group where $R^5$ in the groups represents a hydrogen atom or an alkyl group having 1 to 6 carbon atoms; $R^2$ represents a hydrogen atom, a carboxylic acyl group having 1 to 7 carbon atoms, a tri(1 to 7 carbon atoms)hydrocarbylsilyl group or a group forming an acetal bonding with an oxygen atom of a hydroxy group; $R^3$ represents a straight or branched alkyl group having 3 to 10 carbon atoms, a cycloalkyl group having 4 to 7 carbon atoms, which may be substituted by at least one alkyl group having 1 to 4 carbon atoms, a straight or branched alkenyl group having 3 to 12 carbon atoms, a straight or branched alkynyl group having 3 to 8 carbon atoms, or an alkyl group substituted by a cycloalkyl group having 5 to 8 carbon atoms.

* * * * *